United States Patent [19]

Barendsz et al.

[11] 4,120,754
[45] Oct. 17, 1978

[54] DETECTION OF ALKYLATING COMPOUNDS

[75] Inventors: Anton Willem Barendsz, Katwijk aan Zee; Cornelis De Borst, Delft; Alfred Johannes Antonius Post, Alphen aan de Rijn; Joannes Schimmel, Delft, all of Netherlands

[73] Assignee: Nederlandse Organisatie voor Toegepast-Natuurwetenschappelijk Onderzoek ten behoeve van de Rijksverdediging, The Hague, Netherlands

[21] Appl. No.: 737,189

[22] Filed: Nov. 1, 1976

[30] Foreign Application Priority Data

Oct. 4, 1975 [NL] Netherlands ............... 7512939

[51] Int. Cl.² .......................................... G01N 31/14
[52] U.S. Cl. ..................... 195/99; 195/103.5 R; 195/127; 260/502.4 R
[58] Field of Search .............. 195/99, 103.5 R, 127

[56] References Cited

U.S. PATENT DOCUMENTS 3,049,411  8/1962  Gelman et al. ............. 195/103.5 R
3,689,224  9/1972  Agnew et al. .............. 195/103.5 R Primary Examiner—Raymond N. Jones
Assistant Examiner—C. A. Fan
Attorney, Agent, or Firm—Hammond & Littell

[57] ABSTRACT

Alkylating agents such as the sulphur and nitrogen mustard gases react with the silver salts of dialkyl or diaryl substituted thiophosphoric acids at ambient temperature, thereby producing cholinesterase-inhibiting compounds. This new reaction is applied to a few prior art detection reactions and determination procedures of cholinesterase-inhibiting compounds.

5 Claims, 3 Drawing Figures

DETECTION OF ALKYLATING COMPOUNDS

BACKGROUND OF THE INVENTION

The application relates to a method and devices for the detection and/or determination of alkylating compounds, in particular of sulphur and nitrogen mustard gases.

The use of p-(4-nitrobenzyl)pyridine (NBP) as an analytic reagent for the detection of alkylating compounds is known in the art. Because many potential chemical warfare agents have alkylating properties this reaction has extensively been examined, in particular for the detection of mustard gases. Application of NBP in detection agents for mustard gases has never been quite satisfactory, however. The detection reaction is cumbersome, poorly sensitive and specific, temperature-dependent, while the reagents are poorly stable on prolonged storage. It is known in this field of art that additions like mercury cyanide, sodium perchlorate, sodium diethyl-dithiocarbamate and ethyl acetoacetate can be used to improve these qualities. Also by using nickel(II)-tetrakis p-(4-nitrobenzyl)-pyridine perchlorate complex on activated silica gel in a test tube, the said qualities need to be improved.

Also other reagents are suggested to replace NBP in the determination of alkylating agents; in particular with pyridine-4-carboxaldehyde 2-benzothiazolyl hydrazone, iodine and 1-iodo-butane might be detected very sensitively.

Nerve gases, which form a group of potential chemical warfare agents, possess, just as the organic phosphor insecticides and carbamates, which both are gaining ever-increasing economic importance, the property of acting as cholinesterase-inhibitors. Frequent use is made of this property for the detection of these compounds.

The anticholinesterases are brought into contact with the enzyme cholinesterase. After a certain incubation-time the remaining activity of the enzyme is measured by means of application of a substrate. The enzyme catalyses the hydrolysis of this substrate. Upon hydrolizing, the components to be measured are formed. When applying chromogenous substrates such as 2,6-dichloro indophenyl-acetate(DIBIA), immediately a blue coloured product is formed. Upon application of substrates such as α-naphthyl acetate, α-naphthol and acetic acid are formed. In so doing, the change in pH can be measured or the production of α-naphthol can be measured by adding "Fast Blue B-salt", which with α-naphthol forms a red-violet colour (see, for instance West-German Patent Application No. 2.062.710.

BRIEF SUMMARY OF THE INVENTION

It is the object of the invention to develop detection systems that enable the detection, both qualitatively and quantitatively, of alkylating compounds, such as the sulphur and nitrogen mustard gases, by means of an enzymatic reaction, in so doing, use being made of cholinesterase. Moreover, the reaction may be applied in a continuously operating detection device.

This object could be achieved after the discovery that various alkylating compounds, among which mustard gases, at ambient temperature quickly react with the silver salts of some dialkyl thiophosphoric acids, thus forming cholinesterase-inhibiting organic phosphor compounds.

Because these silver salts themselves are not cholinesterase-inhibiting, various qualitative as well as quantitative detection and analyzing methods have now been developed in a simple way, such as a qualitative enzymatic alarm device, qualitative enzymatic detection systems implemented both in test tubes and on test papers and quantitative enzymatic analysis methods.

Therefore present invention enables the simultaneous detection in analogous detection systems of both nerve gases and mustard gases. If the enzymatic reaction is carried out both with and without addition of the silver salt, respectively, then an immediate differentiation between both groups of chemical warfare agents and/or agricultural chemicals is possible.

The invention is characterized in that the alkylating compounds that are to be determined and/or detected are brought into contact with a silver salt of a thiophosphoric acid, having the general formula:

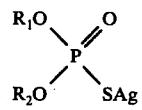

in which $R_1$ and $R_2$ represent an alkyl radical, having 1°–10° C. atoms or a cycloalkyl or aryl radical, having a single ring and in that the cholinesterase-inhibiting compounds formed in the process, are detected and/or determined in the way known in the art for these compounds.

BRIEF DESCRIPTION OF THE DRAWING

The drawing shows some devices adapted for detecting alkylating compounds according to the invention wherein.

DETAILED DESCRIPTION OF THE INVENTION

Chemical Principle

Figure 1:
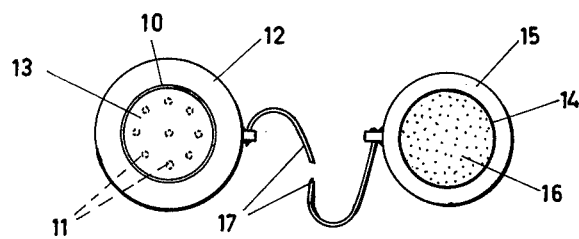
FIG. 1 shows a "press-button" seen from above.

The general structural formula of both phosphoric and thiophosphoric compounds inhibiting the enzyme cholinesterase is as follows:

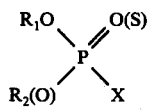

In it $R_1$ and $R_2$ are alkyl, dialkylamino, or aryl groups and X is the group called "leaving group", this is the group that is split off during inhibition of the enzyme cholinesterase. As an example of such a group, $-S-CH_2-CH_2-S-C_2H_5$ can be mentioned, which occurs in the cholinesterase-inhibiting insecticide Systox. Very generally speaking, cholinesterase-inhibiting compounds can be prepared by reacting the salt of a thiophosphonic acid, thiophosphoric acid, respectively, with an alkyl halide.

The alkylating properties of mustard gases offer the opportunity of forming cholinesterase-inhibiting products via the reaction with a salt of a thiophosphonic or thiophosphoric acid, respectively. The application of such a reaction in detection and analyzing methods requires, however, that the starting materials are not cholinesterase-inhibiting, that the conversion proceeds very quickly, also at ambient temperature, and that the products formed do strongly inhibit the enzyme cholinesterase. It has been found that the silver salts of dialkyl thiophosphoric salts meet these requirements and even in the dry state at ambient temperature react very quickly with mustard gases, while forming products that are highly cholinesterase-inhibiting.

After the reaction of sulphur mustard gas (bis-(chloroethyl)-sulphide) with the silver salt of dimethyl thiophosphoric acid, the following cholinesterase-inhibiting products could be identified:

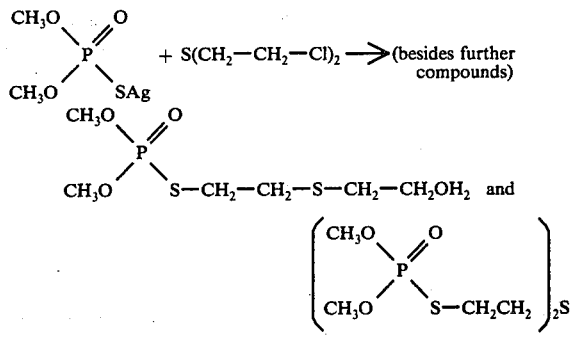

The silver of the said di-substituted thiophosphoric acids can be prepared in a simple way by reaction of the corresponding ammonium salts with silver nitrate in an aqueous mileu. As an example the preparation of di-n-propyl thiophosphoric acid-silver is described.

EXAMPLE I.

The preparation of the silver salt of di-n-propyl thiophosphoric acid.

The ammonium salt of di-n-propyl hydrogen thiophosphoric acid is prepared by reacting di-n-propylphosphite with dry ammonia and sulphur in a solution of dichloro ethane. The product has a melting point of 148° C., while the output of the reaction is 90-95%. Thereupon at ambient temperature a solution of 11.9 g of silver nitrate (pro analysis quality) in 300 ml of water is added to a solution of 15 g of the ammonium salt of di-n-propyl hydrogen thiophosphoric acid in 500 ml of water. Immediately after the addition the silver salt desired precipitates. The silver salt is filtered off and dried over phosphorus pentoxide. After recristallization from ethanol 13.5 g (65%) of the pure product (decomposes upon melting) are obtained.

Applications of the disubstituted thiophosphoric silver salts

The silver salts of the disubstituted thiophosphoric acids in the solid and/or dissolved state, at ambient temperature react quickly with the alkylating compounds to be detected, i.e. the sulphur and nitrogen mustard gases. Because the starting materials, notably the silver salts themselves, are not cholinesterase-inhibiting and the reaction products inhibit the enzyme cholinesterase, these alkylating compounds can be detected by means of an enzymatic reaction. So, these silver salts can be applied in various ways in alarm and detection equipment, with which the presence of the alkylating compounds can be confirmed or they can be used as reagents in quantitative analytical determination methods.

The silver salt of dimethyl thiophosphoric acid is somewhat light sensitive and only slowly dissolves in ethanol. The silver salts of diethyl and diisopropyl thiophosphoric acid form relatively weakly inhibiting compounds. Because the products formed with the silver salt of di-n-propyl thiophosphoric acid show a stronger inhibiting action as the products formed with the silver salt of di-n-butyl thiophosphoric acid, for the analyzing and detection techniques, preferably, use is made of the silver salt of di-n-propyl thiophosphoric acid.

As parts of the invention the following applications can be described:
1. A quantitative analysis of mustard gas in water;
2. A qualitative detection of mustard gas in water;
3. A quantitative determination of mustard gas in air;
4. Simple means of detection for the detection of mustard gas in air;
5. An alarm upon the detection of the presence of mustard gas in the air;

Though the stated enzymatic analyzing and detection techniques are characterized by a great selectivity and sensitivity, it will be clear that if besides mustard gases there are also cholinesterase-inhibiting compounds, e.g. nerve gases or organic phosphor insecticides, these also will be detected. In order to be able to differentiate then a blank reaction will have to be carried out, by which is understood that, in so doing, no silver salt of an organic thiophosphoric acid is applied.

The method and devices according to the invention are elucidated by means of the examples below, and illustrated in the drawing.

EXAMPLE II.

Quantitative analysis of mustard gas in water 6 ml of an ethanol solution, in which 120 mg of the silver salt of di-n-propyl thiophosphoric acid are suspended, are added to 2 ml of an aquous solution of mustard gas of unknown concentration. The solution (or suspension, if any) is shaken thoroughly and put aside for 1 to 5 minutes at a temperature of 25° C. This solution is mixed with 40 ml of 0.2 M phosphate buffer (pH=7.5).

Of the solution obtained, 4 ml is pipetted into a test tube and is put in a bath maintained at 25° C. To this is added 1 ml of an enzyme solution (0.75 mg of butryl cholinesterase (approximately 2.5 E) in 10 ml of 0.2 M phosphate buffer solution), (pH=7.5). After 2-5 minutes 1 ml of an aqueous α-naphthyl acetate solution (prepared as stated further below), is added and 2 minutes thereafter 1 ml of a diazo blue-lauryl sulphate solution (Fast Blue B-salt) is added (400 mg diazo blue is dissolved in 100 ml of water; the two solutions are joined, filtered off after 10 minutes and put aside in the dark).

After 3 minutes the extinction is measured at 600 nm. By means of calibration curves obtained with mustard gas solutions of known concentrations, with this quantitative analyzing method the concentration can be determined accurately in the range of 0.05-5 mg/l for sulphur mustard gas and 0.02-2 mg/l for the nitrogen mustard gas, tris (2-chloroethyl) amine.

The α-naphthyl acetate solution applied in this example is prepared by dissolving 559 mg of α-naphthyl acetate in 100 ml of acetone and diluting the solution obtained, with water to 20 times its volume.

EXAMPLE III.

Qualitative detection of mustard gas in water 6 ml of alcohol in which 120 mg of silver salt of di-n-propyl thiophosphoric acid has been suspended are added to 2 ml of a water sample containing a mustard gas. After the solution (suspension, if any) has been thoroughly shaken for 3 minutes, again 40 ml of the water sample are added to it and the whole is quickly mixed. Into this solution a part of an enzyme paper, impregnated with butyryl cholinesterase, Tris-buffer and Tergitol 15-S-12 as a wetting agent, is dipped until this is entirely wetted (approximately 10 to 15 sec). After a 10 minutes' incubation time the enzyme paper is for 1 minute pressed together with a substrate paper (Whatman I-paper impregnated with 2,6-dichloro indophenyl acetate). Immediately thereafter the colour of the enzyme paper is evaluated. If the enzyme paper contains 0.2 E/cm$^2$ of butyryl cholinesterase the following detection limits are found:

|  | enzyme paper just not coloured | enzyme paper less blue than blank |
|---|---|---|
| sulphur mustard gas | 2 mg/l | 0.2 mg/l |
| nitrogen mustard gas tris- (2-chloroethyl) amine | 1 mg/l | 0.1 mg/l |

EXAMPLE IV.

Quantitative determination of mustard gas in air

During 30 minutes the air to be examined is sucked with an air velocity of 150 ml/min through a small wash bottle which is filled with 5 ml of methyl isobutyl carbinol. Of the resulting liquid 1 ml is added with a pipet to 5 ml of ethanol in which 100 mg of the silver salt of di-n-propyl thiophosphoric acid has been suspended. Thereupon to this solution 2 ml of distilled water is added. The solution (suspension, if any) is shaken thoroughly and put aside for 1 to 5 minutes at a temperature of 25° C. Next the procedure as described in Example II is followed from the moment when 40 ml of 0.2 M phosphate buffer (pH=7.5) are added. In this manner, the quantitive analyzing method described allows the mustard gas concentration in air flows to be determined in the range of 0.05–5.5 mg/m$^3$ for sulphur mustard gas and of 0.02–2 mg/m$^3$ for the nitrogen mustard gas, tris (2-chloroethyl) amine.

EXAMPLE V.

A simple means of detection for the detection of mustard gas in air

During 2 minutes air that contains mustard gas, is sucked with a capacity of 20 l/min. through a dry reagent paper. The reagent paper had been prepared by impregnating a filter paper known as Ederol 281-fleece-fibre paper successively with 10 g of silica gel in 100 ml of water, 200 mg of the silver salt of di-n-propyl thiophosphoric acid in 100 ml of ethanol, and a butyryl-cholinesterase solution in water, whereby a reagent paper is obtained, having an enzyme activity of 0.15 to 0.20 E/cm$^2$. (1 E = 1 μmol of acetylcholine/min, pH 7.5, 25° C., see Report Comm. Enzymes, Pergamon Press, N.Y., 1961, page 8).

After sucking, for 2 minutes the inhibitor is allowed to form. Next, the reagent paper is wetted with a 0.1 M Tris-buffer (pH = 8.0) in water and then an incubation time of 2 minutes is observed. Next, the enzyme paper is for 1 minute contacted with a substrate paper (Whatman I-paper impregnated with 2,6-dichloro indophenyl acetate) and, finally, the colour formed on the enzymatic paper is evaluated. The paper will be colourless or light pink if the concentration of sulphur mustard gas in the air flow is greater than or equal to 0.06 mg/m$^3$, and greater than or equal to 0.03 mg/m$^3$, respectively, for the nitrogen mustard gas, tris (2-chloroethyl) amine, respectively. In case of lower concentrations, there will be a remnant activity present of the enzyme, so that on the enzyme paper a blue colour is formed. (Tris, (in the buffer) stands for tris(hydroxymethyl) amino methane).

Figure 2:
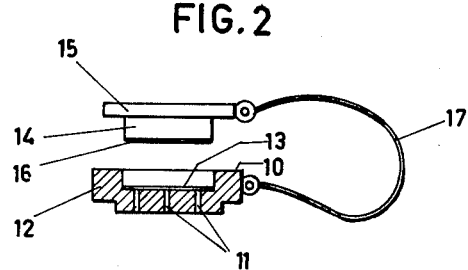
FIG. 2 shows the same "press-button" from aside and FIG. 3 shows a test tube prepared for the application of the detection reaction of the present invention.

The reagent paper mentioned in this example can advantageously be inserted into a "detection press-stud" as shown in FIGS. 1 and 2 and previously described in West German Patent Application No. 2,062,710.

The socket part indicated as "stud" comprises a stud body 12 provided with some perforations 11. Paper 13, impregnated with silica gel, silver salt and cholinesterase, is mounted on the inner side of the perforated front wall of the stud body which front wall is provided with a raised edge 10. This raised wall on the one hand enables the attachment to a sucking device and on the other hand the pressing on to it of the counter body. This counter body, press-member 15, showing a raised part 14, fits into edge 10 of stud body 12. On this raised part 14 substrate paper 16 is mounted, which in this way can be brought into contact with enzyme paper 13. The two parts of the detection stud are advantagously, mutually connected by a flexible rope or chord 17, though this is not essential.

EXAMPLE VI.

Alarming when mustard gas is present in the air

For the detection of nerve gases, alarming equipment is known in the art with which within a very short time a warning is given off when a toxic concentration is present in the surrounding atmosphere.

Mostly with such an equipment, air is sampled on a continuously moving conveyer belt that has been impregnated with silica gel.

After the belt has been successively wetted with a cholinesterase solution and a substrate solution, colour formation will take place on the conveyer belt in proportion as cholinesterase-inhibiting compounds are present in the atmosphere. A colour difference can be detected by measuring with photocells light reflecting on the belt. If the belt, impregnated with silica gel is also impregnated with the silver salt of di-n-propyl thiophosphoric acid then the alarming function of the equipment for nerve gases is extended to an alarming function for mustard gases.

EXAMPLE VII.

Test tubes for the detection of mustard gases in air

Figure 3:
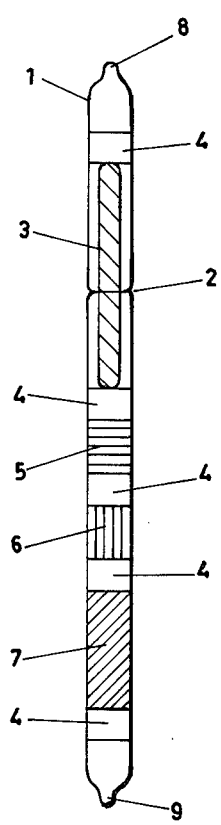

In the copending U.S. patent application Ser. No. 743,556, filed Oct. 21, 1976, and claiming benefit of the Netherlands application Ser. No. 75 12320, a test tube has been described for the detection of gases with cholinesterase-inhibiting action as shown in FIG. 3, in tube 1 being present in the following order;

(a) an ampoule 3 with a buffer solution, of pH 7.5–8.0;
(b) a dry preparation 5 of a chromogenous substrate and a filler, in particular a freeze-dried mixture of 2,6-dichloroindophenyl acetate (DIBIA) and partially hydrolized gelatine which accelerates the dissolution of the substrate;

(c) a dry preparation 6 of a cholinesterase and a filler, in particular of butryl cholinesterase and partially hydrolized gelatine which accelerates the dissolution of the enzyme; and (d) as an indicator layer an adsorbing agent 7 in particular silica.

For adapting the said test tube to the detection of mustard gases now adsorbing agent 7 can be impregnated with a suitable amount of the silver salt of a thiophosphoric acid, preferably of di-n-propyl thiophosphoric acid.

In the tube the zones with the various preparations are separated by partitions 4 permeable to gases and liquids. At their ends the tubes are sealed with tops 8 and 9 to be broken off before the reaction. Thereupon the tube is connected to a pump and by means of a specific number of pump strokes a certain amount of the air that may be polluted with the gases to be detected is sucked through the tube.

Through the test tube 2 1 of mustard-gas containing air is sucked with a particular reciprocating pump by means of 20 pump strokes. The mustard gas is captured on the impregnated silica (100 mg), situated in the test tube. The impregnated silica has been prepared by suspending 10 g of well-dried finely divided silica into 20 ml of ethanol in which 40 mg of the silver salt of the di-n-propyl thiophosphoric acid has been dissolved and whereupon the silica is dried by evaporation of the ethanol.

After sucking through the sample of air, the inhibitor is allowed to form for 4 minutes. As a result of the specific build-up of the test tube, viz. the impregnated silica layer, an enzyme preparation, a substrate preparation and an ampoule filled with 0.2 ml of buffer solution (e.g. 0.1 M tris-buffer, pH 8) the silica layer can directly be wetted with the buffer/enzyme/substrate solution by breaking the ampoule lying on top of it, the substrate as well as the enzyme dissolving immediately in the liquid flowing down. After 2 minutes the colour formed on the silica layer is evaluated.

The silica will be colourless or light pink if the concentration of sulphur mustard gas in the air sampled is greater than or equal to 0.2 mg/m$^3$ and for the nitrogen-mustard gas, tris (2-chloroethyl) amine, if it is greater than or equal to 0.1 mg/m$^3$, respectively. In case of lower concentrations a remnant activity of the enzyme will be present, so that on the silica layer a light blue to bright blue colour will be formed.

We claim:

1. A combined detection set for the detection of sulphur and nitrogen mustard gases, wherein the mustard gases to be determined are brought into contact with a silver salt of a thiophosphoric acid having the formula

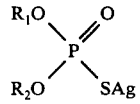

in which $R_1$ and $R_2$ are members selected from the group consisting of alkyl having 1 to 10 carbon atoms, cycloalkyl and aryl having one ring under conditions whereby cholinesterase-inhibiting compounds are produced, and wherein the cholinesterase-inhibiting compounds are detected and/or determined by a chromogenous substrate for these compounds, wherein the set comprises:

(a) an adsorbing substrate strip, which successively has been impregnated with:
  (1) a suspension of an adsorbing agent in water,
  (2) a suspension or solution of said silver salt of the thiophosphoric acid in an organic solvent, and
  (3) a cholinesterase solution in water, in an amount whereby the desired enzymatic activity on the substrate strip is obtained;
(b) an aqueous buffer solution, having a pH 7.5–8, and
(c) a second strip, impregnated with a cholinesterase-inhibiting detection amount of a chromogenous substrate.

2. A combined detection set according to claim 1, wherein, besides the aqueous buffer solution (b), it contains:
(a) a strip of reagent paper which successively has been impregnated with
  (1) suspension of silica gel in water,
  (2) a suspension or solution of the silver salt of di-n-propyl thiophosphoric acid in an organic solvent, and
  (3) a butyryl cholinesterase solution in water, such that an activity of 0.15 to 0.20 E/cm$^2$ is obtained; and said second strip (c) is a strip of reagent paper impregnated with 2,6-dichloro indophenyl acetate.

3. A detection set according to claim 1, wherein said substrate strips are mounted in such a manner whereby the substrate strips can be brought into contact with each other.

4. A test tube for the detection of sulphur and nitrogen mustard gases, wherein the mustard gases to be determined are brought into contact with a silver salt of a thiophosphoric acid having the formula

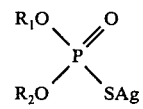

in which $R_1$ and $R_2$ are members selected from the group consisting of alkyl having 1 to 10 carbon atoms, cycloalkyl and aryl having one ring under conditions whereby cholinesterase-inhibiting compounds are produced, and wherein the cholinesterase-inhibiting compounds are detected and/or determined by a chromogenous substrate for these compounds, wherein the tube contains successive zones with:
(a) an ampoule with an aqueous buffer solution of a pH 7.5–8,
(b) a dry preparation of a chromogenous substrate and an agent that accelerates its dissolution in said aqueous buffer solution,
(c) a dry preparation of a cholinesterase and an agent that accelerates its dissolution in said aqueous buffer solution, and
(d) silica, impregnated with the said silver salt of a thiophosphoric acid.

5. A test tube according to claim 4, wherein the tube successively contains zones comprising:
(a) an ampoule with an aqueous buffer solution, having a pH 7.5–8,
(b) a dry preparation of 2,6-dichloro indophenyl acetate and partially hydrolyzed gelatine,
(c) a dry preparation of butyryl cholinesterase and partially hydrolyzed gelatine, and
(d) silica, impregnated with the silver salt of di-n-propyl thiophosphoric acid.

* * * * *